United States Patent [19]

Wang

[11] Patent Number: 6,125,704
[45] Date of Patent: Oct. 3, 2000

US006125704A

[54] ULTRASONIC TECHNIQUE FOR INSPECTION OF WELD AND HEAT-AFFECTED ZONE FOR LOCALIZED HIGH TEMPERATURE HYDROGEN ATTACK

[75] Inventor: Weicheng David Wang, Katy, Tex.

[73] Assignee: Shell Oil Company, Houston, Tex.

[21] Appl. No.: 09/008,016

[22] Filed: Jan. 16, 1998

[51] Int. Cl.$^7$ ................................................... G01N 29/06
[52] U.S. Cl. ................................................. 73/602; 73/600
[58] Field of Search ........................... 73/602, 620, 622, 73/624, 628, 629, 597–600

[56] References Cited

U.S. PATENT DOCUMENTS

| | | | |
|---|---|---|---|
| 3,996,791 | 12/1976 | Niklas et al. | 73/602 |
| 4,393,711 | 7/1983 | Lapides | 73/592 |
| 4,428,235 | 1/1984 | Sugiyama | 73/579 |
| 4,685,334 | 8/1987 | Latimer | 73/599 |
| 4,890,496 | 1/1990 | Birring et al. | 73/597 |
| 5,404,754 | 4/1995 | Wang | 73/602 |
| 5,445,029 | 8/1995 | Falsetti et al. | 73/609 |
| 5,591,913 | 1/1997 | Tucker | 73/628 |

*Primary Examiner*—Hezron Williams
*Assistant Examiner*—Rose M. Miller

[57] ABSTRACT

The technique is based on comparing the spectral response of the "suspect" signal with that of a reference signal. The "suspect" signal is a signal detected in the weld heat-affected zone by a high-frequency (10 MHz), angle-beam (typically 45 degree) shear wave transducer operated in the pulse-echo mode. The reference signal is taken from the base metal next to the weld or heat-affected zone with two matched transducers of the same kind as the pulse-echo transducer but operated in the pitch-catch mode. The two signals are gated and Fast Fourier Transformed to the frequency domain for comparison. Relative to the reference spectrum, the high temperature hydrogen attack spectrum has an amplitude which increases with an increase of frequency, while welding defects and inclusions have the same frequency dependence as the reference spectrum. Therefore, localized high temperature hydrogen attack can be easily differentiated from other defects due to its unique spectral response.

5 Claims, 10 Drawing Sheets

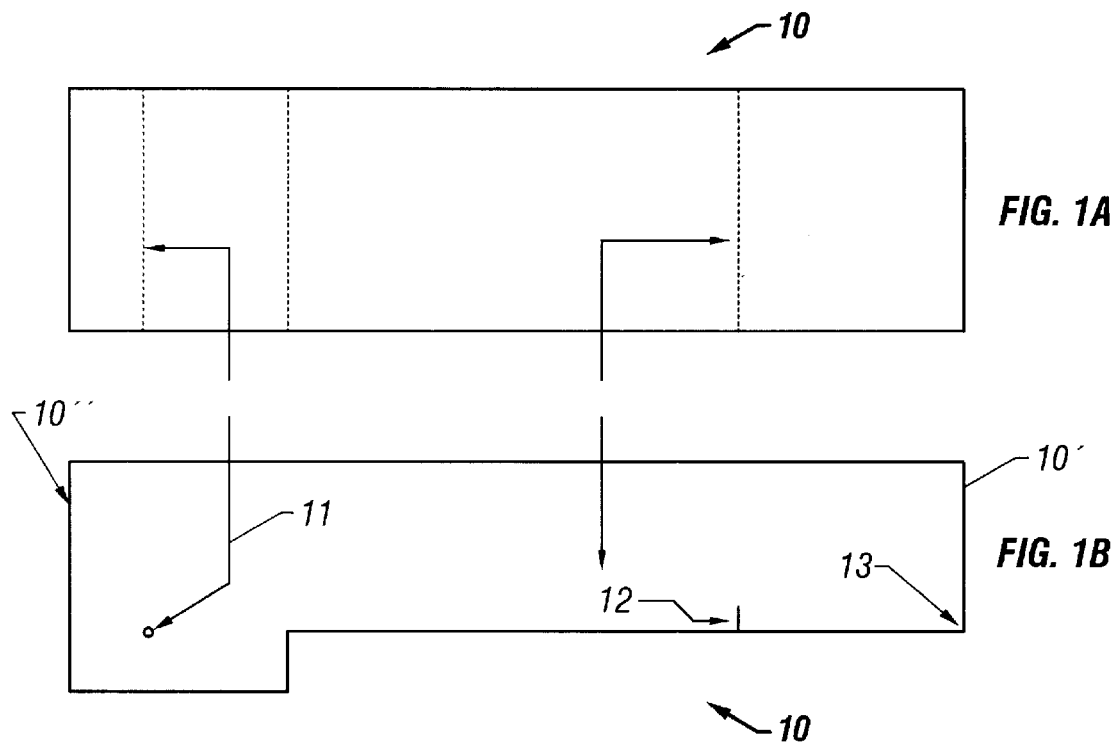
FIG. 1A
FIG. 1B
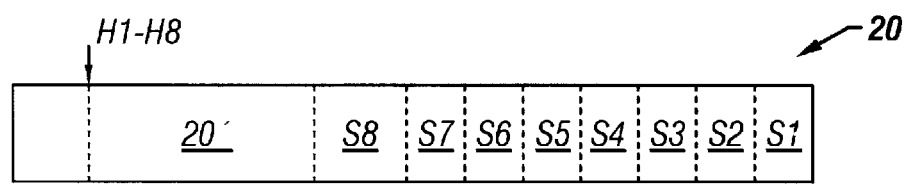
FIG. 2A
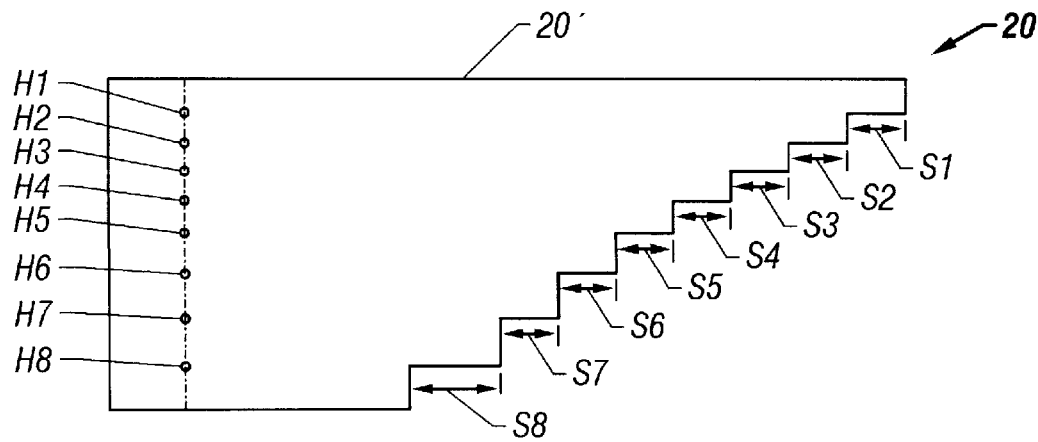
FIG. 2B

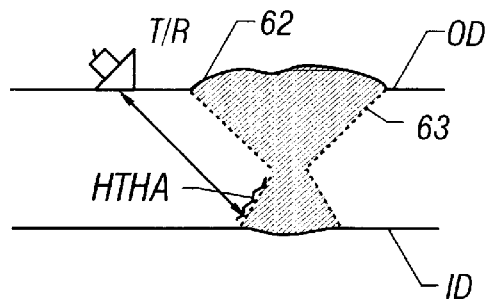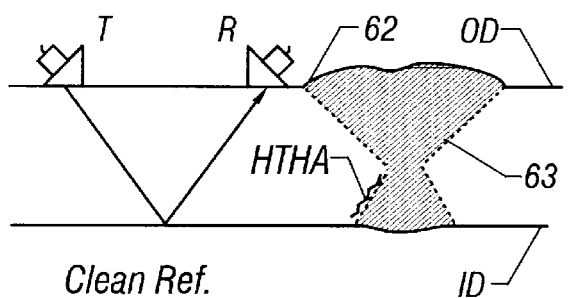
FIG. 15A  FIG. 15C
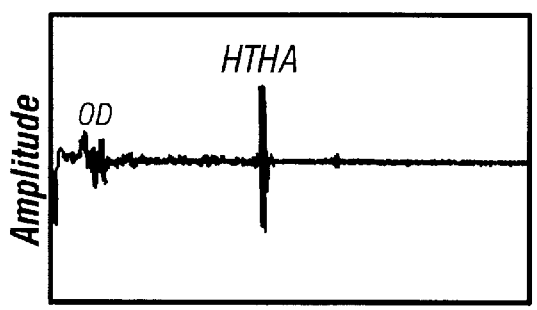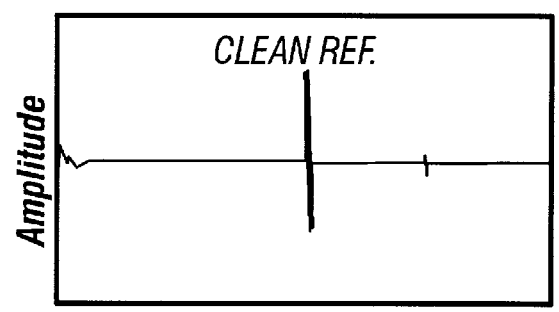
FIG. 15B  FIG. 15D

ULTRASONIC TECHNIQUE FOR INSPECTION OF WELD AND HEAT-AFFECTED ZONE FOR LOCALIZED HIGH TEMPERATURE HYDROGEN ATTACK

BACKGROUND OF THE INVENTION

1. Field of the Invention

This invention is an ultrasonic Angle Beam Spectrum Analysis (ABSA) technique for differentiation of localized High Temperature Hydrogen Attack (HTHA) in welds and any heat-affected zone (HAZ) from other defects in the same area, e.g., welding defects (including porosity, slag, undercut, lack of fusion, etc.) and inclusions.

2. Description of the Prior Art

Previous HTHA inspection techniques using straight-beam ultrasonic transducers can detect and characterize volumetric HTHA in weld metal and base metal, but cannot detect or characterize localized HTHA in a weld or HAZ (weld/HAZ. See U.S. Pat. No. 5,404,754 which is incorporated herein by reference.

Prior to the instant invention, there was no nondestructive technique that could identify localized HTHA in a weld/HAZ from the external surface of a pipe or a pressure vessel.

Conventional, ultrasonic techniques using angle-beam transducers to inspect a weld/HAZ can detect localized HTHA when operated at a high sensitivity level, but cannot differentiate localized HTHA from welding defects and inclusions that are also detectable at the high sensitivity level.

SUMMARY OF THE INVENTION

The technique is based on comparing the spectral response of the "suspect" signal with that of a reference signal. The "suspect" signal is a signal detected in the weld/HAZ region by a high-frequency (10 MHz), angle-beam (typically 45 degree) shear wave transducer operated in the pulse-echo mode. The reference signal is taken from the base metal next to the weld with two matched transducers of the same kind as the pulse-echo transducer but operated in the pitch-catch mode. The two signals are gated and Fast Fourier Transformed (FFT) to the frequency domain for comparison. Relative to the reference spectrum, the HTHA spectrum has an amplitude which increases with an increase of frequency, while welding defects and inclusions have the same frequency dependence as the reference spectrum. Therefore, localized HTHA can be easily differentiated from other defects due to its unique spectral response.

BRIEF DESCRIPTION OF THE DRAWINGS

FIGS. 1A and 1B show plan and side elevation views of a calibration block which may be used for transducer selection, system calibration, and alternative threshold settings.

FIGS. 2A and 2B show plan and side elevation views of a calibration block which may be used for threshold setting.

FIGS. 15A–D show the ultrasonic technique for detecting localized high temperature hydrogen attack in a weld/HAZ.

DETAILED DESCRIPTION OF PREFERRED EMBODIMENTS

FIGS. 1A and 1B show a calibration block which may be used for transducer selection, system calibration and alternative threshold setting. The purpose of using a calibration block is primarily to make sure that there is enough sensitivity of the system to high temperature hydrogen attack in a weld/HAZ so that when the inspection is performed, the signal can be detected. The next step is to determine what kind of signal is detected because the signal could be caused by hydrogen attack or it could be caused by a welding defect, such as porosity, slag, lack of fusion or undercut in the weld. The calibration block is to ensure having the proper sensitivity level to detect the damage that is present. Calibration is required each time just prior to making an inspection in the field to ensure that the system is not damaged because of shipping, i.e., to make sure the electronic portion is functional.

FIGS. 2A and 2B show a calibration block for ensuring that the system has the required poly-sensitivity level. The difference between FIGS. 1 and 2 is that the calibration block of FIG. 2 clearly considers the effect of attenuation in the material. For that reason there are different defects having different depths in this calibration block. The calibration blocks are made of the same material as the pipe or equipment to be tested. The calibration procedure is good for all different grades of steel. The calibration block of FIG. 2 ensures that attenuation effects due to the thickness of the material is taken into account so that when thick-walled vessels are inspected, the thickness of the material is penetrated with sound beams to detect defects on the inside diameter (ID) surface of the vessel under test. Calibration ensures that sound beams can penetrate the wall of the pipe or vessel and return. In summary, both calibration blocks of FIGS. 1 and 2 are to make sure the system is calibrated so as to have enough sensitivity for detection.

Figure 3:
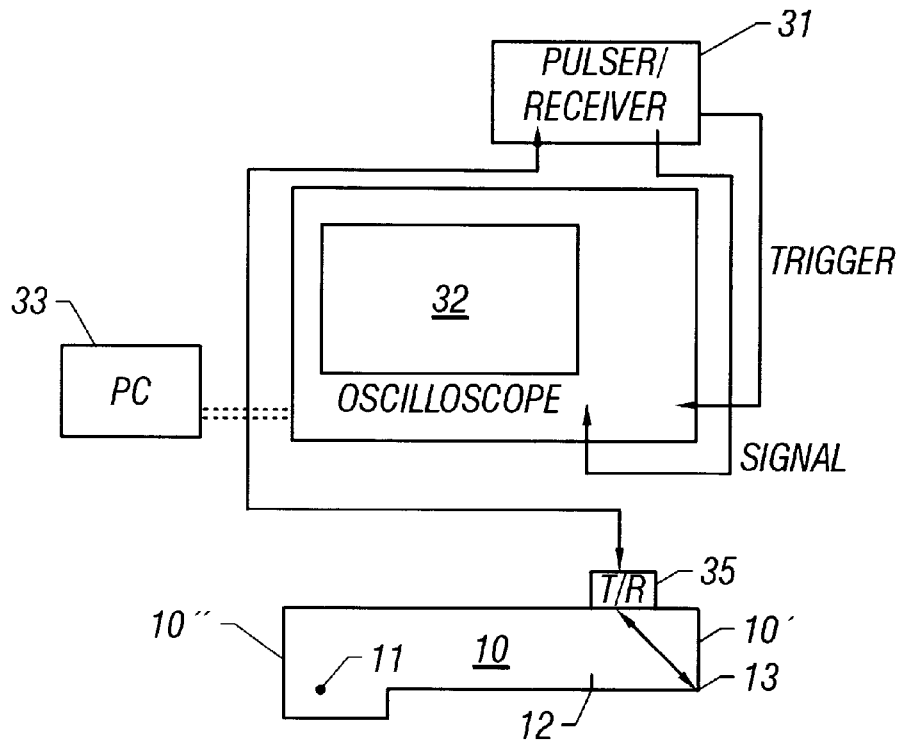
FIG. 3 shows the equipment setup for transducer selection and system calibration.

FIG. 3 shows the equipment setup of the system for transducer selection and system calibration. This shows the equipment required including the pulser/receiver 31, digital oscilloscope 32, PC 33, calibration block 10 and transducer 35, and how they should be connected. This setup is for pulse-echo calibration. Only one transducer 35 is needed for sending and receiving a pulse since the signal echo is received with the same transducer.

Figure 4:
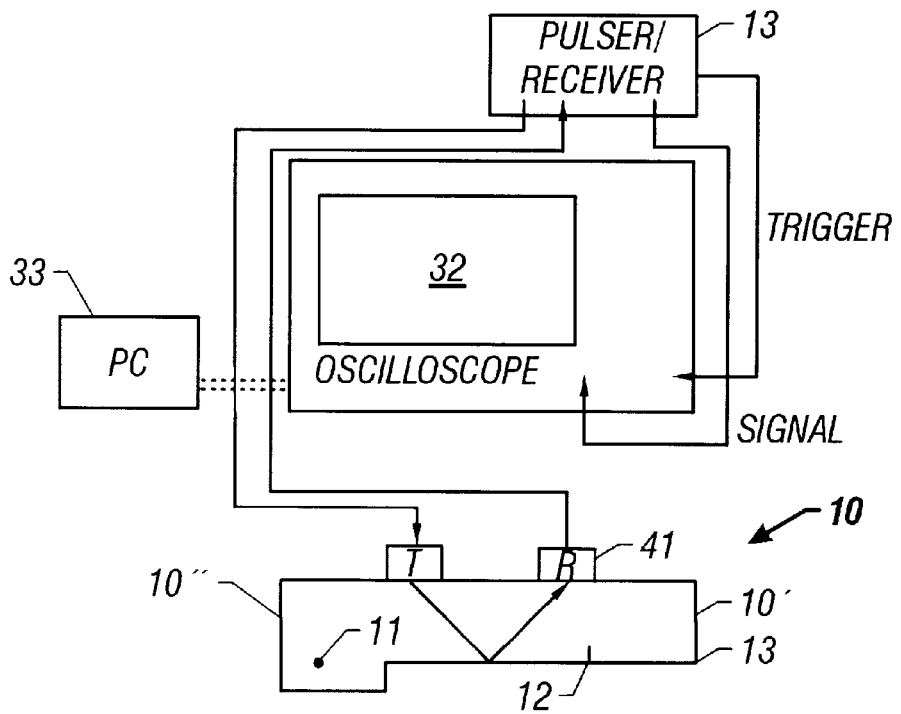
FIG. 4 shows the equipment setup for system calibration.

FIG. 4 shows the calibration setup for pitch-catch. A separate transducer 41 (receiver, R) is required to "catch" the signal pitched by the transmitter 42, T.

Figure 5A:
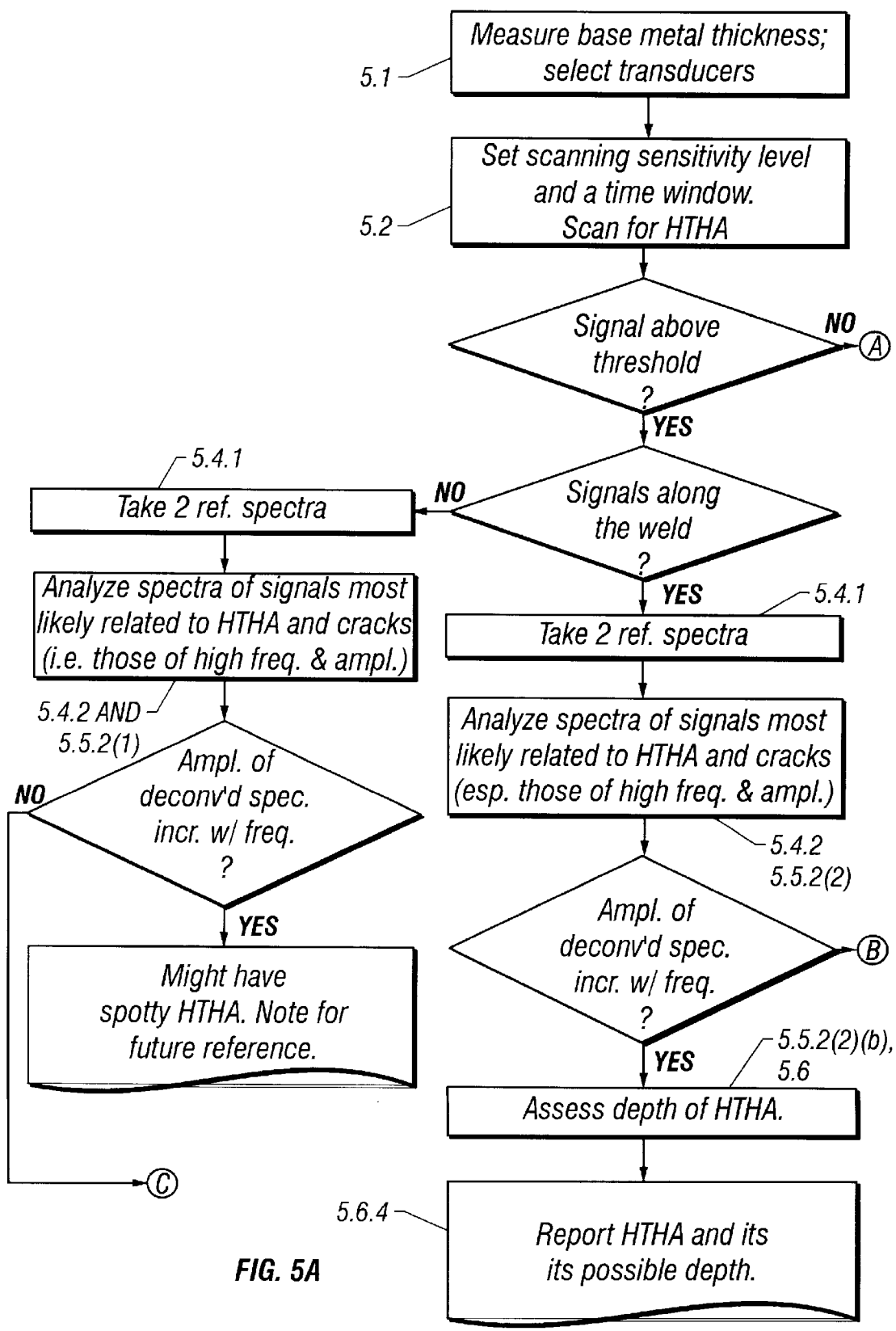
FIG. 5 is a logic tree or flow chart for performing a field inspection according to the invention.
Figure 5B:
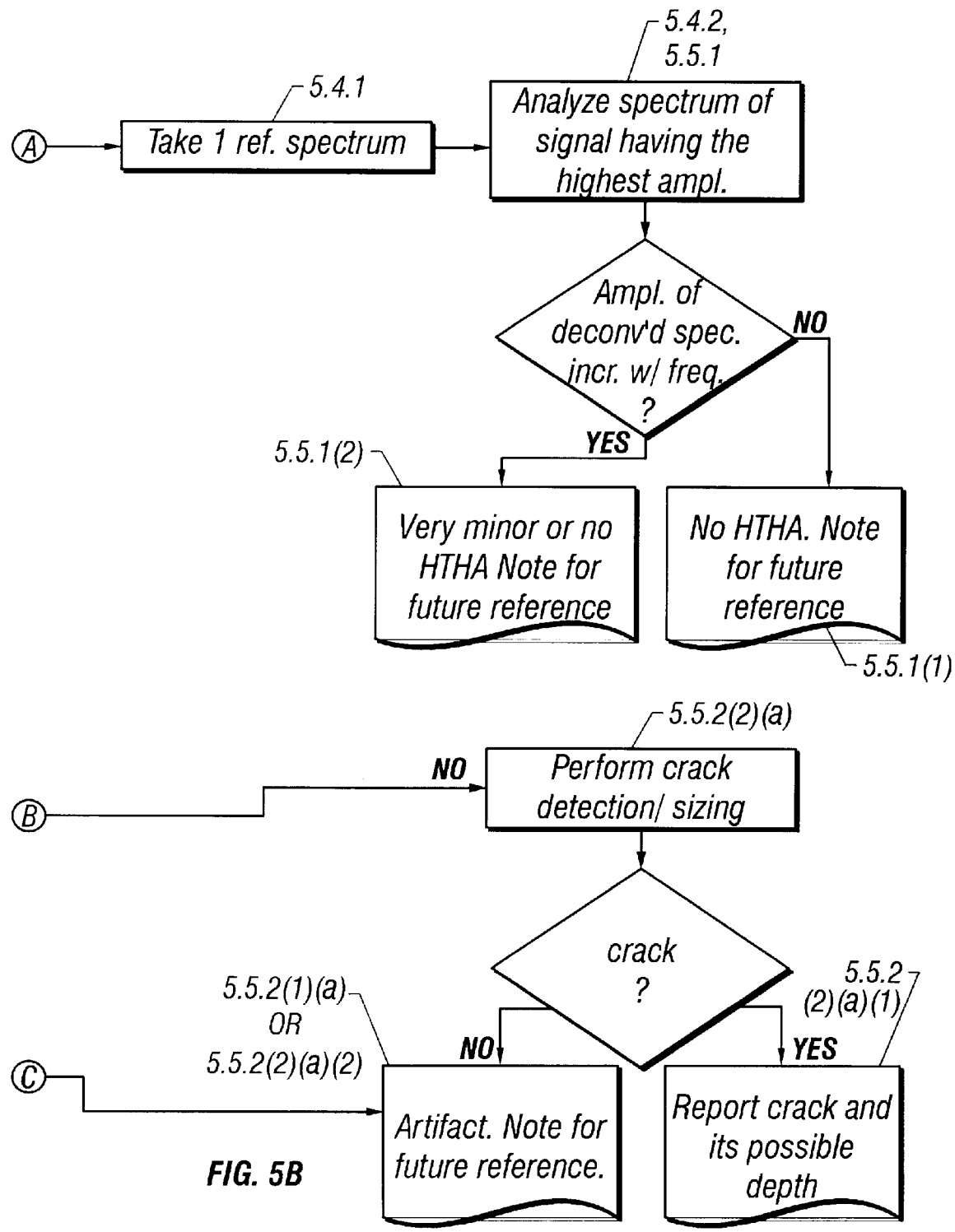

FIG. 5 shows the logic tree used for taking measurements as well as for interpretation of the results of an inspection. This is a guide for proceeding through the various inspection steps and for arriving at the proper conclusions, i.e., it is a graphical presentation of the entire inspection procedure which is later described herein in detail.

DETAILED PROCEDURE

The procedure begins with a measurement of the material thickness. This is done on base metal next to the weld/HAZ undergoing examination. Based on the material thickness, a proper transducer must be selected and focused transducers are required for material thicknesses greater than about 1.2 inches. Different transducers have different focal depth and, by knowing the thickness, a focused transducer can be selected which corresponds to the material thickness. Based on the calibration, detection threshold can be selected as shown in Table 5. The material is scanned to see if a signal can be detected. If signals are detected in the weld/HAZ, it must then be determined whether the signals along the weld are suspect, i.e., above a threshold level. A "suspect" signal may have the characteristics shown in Table 7.

If there is no "suspect" signal, logical route "No" is followed and a single reference spectral analysis is performed. The reference spectrum, which is always taken in the pitch-catch mode, is taken from a clean area using the setup shown in FIG. 4. ABSA of signals of the highest amplitude are taken and are always measured from a pulse-echo measurement as shown in FIG. 3. If the amplitude of deconvolved ABSA signals does not increase with frequency, then there is no hydrogen attack. If the amplitude does increase with frequency, it could be an indication of very minor damage and is simply noted.

When there is a "suspect" signal, logical path "Yes" is followed. It must then be determined whether the "suspect" signals go along the weld. If the "suspect" signal does not go along the weld, i.e., it is a more isolated "suspect" signal, then logical path "No" is followed and two reference spectra are taken as opposed to just one when there were no "suspect" signals. An angle beam spectrum analysis is then performed on the "suspect" signal and the spectrum from the "suspect" signal is compared to the average of the two reference spectra. This process is called deconvolution. If the difference which is deconvolved results in showing an increase of amplitude with an increase of frequency, then following the "Yes" route shows that there might be spotty HTHA. If the amplitude does not increase with frequency, then the "No" route is followed and it is probably not HTHA. It is simply noted in the record that a "suspect" signal has been detected so that at the next inspection the same defect can be reexamined.

If "suspect" signals are detected along the weld, then the "Yes" route is selected and, once again, two reference spectra are taken next to the weld using the pitch-catch measurement setup of FIG. 4. The average of the two reference spectra is then compared to the spectrum of the "suspect" signal. That comparison, which is measuring the difference between the two, will give the deconvolved spectrum. If the amplitude of the deconvolved spectrum increases with frequency, then following the "Yes" path shows that there is possible HTHA and the depths of HTHA must be measured using shear wave and creeping wave transducers. If there is no increase with frequency, then following the "No" path shows that there may be a cracking (macrocracking) problem as opposed to a hydrogen attack fissuring (microcracking) problem. This then requires using crack detection/sizing techniques with shear wave and creeping wave transducers. Depending on that result, either a crack is confirmed—in which case the crack and its possible depth should be reported—or there is no crack and it is just reported as an artifact for future reference in repeated exams.

Figure 6A:
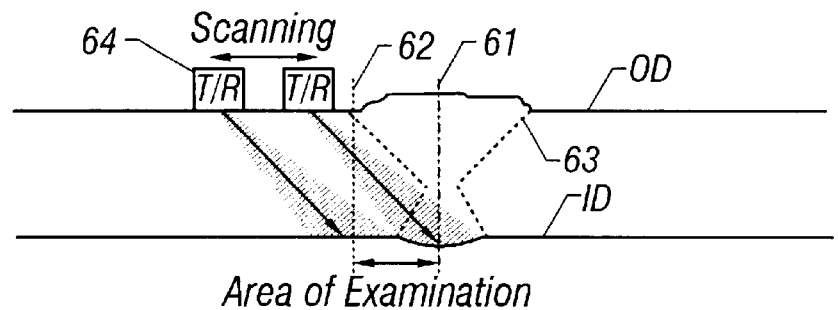
FIGS. 6A and 6B show initial scanning of a double V-joint and single V-joint, respectively, weld/HAZ where the specimen is without internal cladding or weld overlay.

FIG. 6A shows the required scanning area for a Double-V weld joint where there is no internal cladding or weld overlay. The scanned area should cover from the center of the weld 61 to the edge 62 of the top weld toe as a minimum. The weld is the dotted line 63. The top surface usually is the OD surface of the vessel or pipe so the toe of the weld 62 is easily seen. When the sound beam reaches the ID surface, the area from the center of the weld 61 to the outer edge is covered. Depending on the angle of the transducer 64, simple trigonometry will determine where the sound beam is coming from. Single-V weld joints receive the same treatment as shown in FIG. 6B.

Figure 6B:
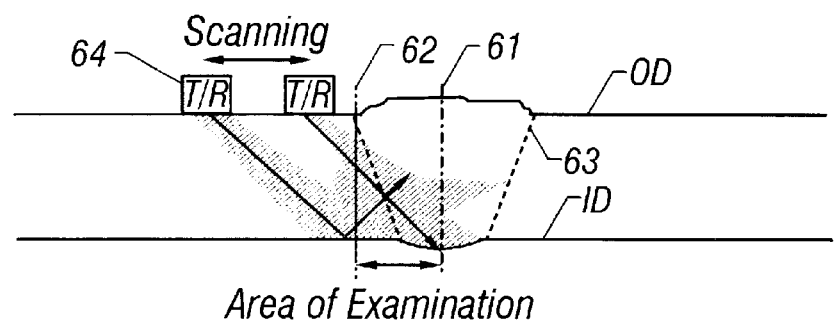
Figure 7A:
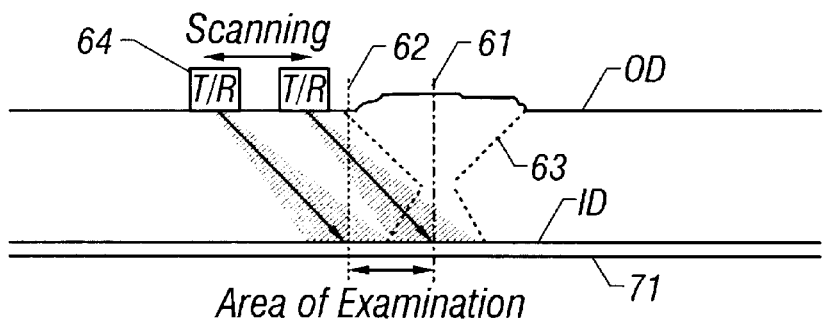
FIGS. 7A and 7B show initial scanning of a double V-joint and single V-joint, respectively, weld/HAZ where the specimen has an internal cladding or weld overlay.
Figure 7B:
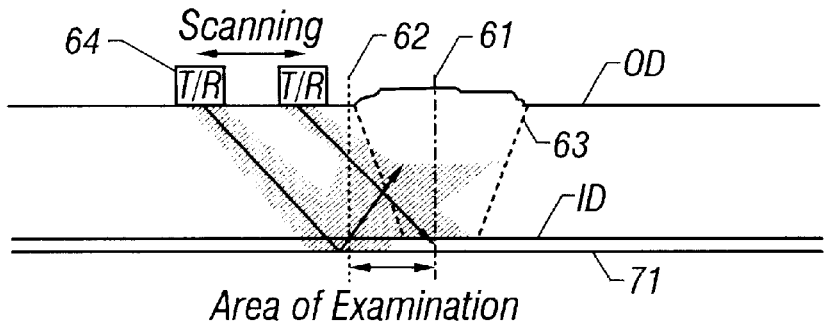

FIGS. 7A and 7B are similar to FIGS. 6A and 6B, respectively, but show the case where there is a weld overlay or cladding 71 on the ID surface of the pipe or vessel being inspected.

Figure 8A:
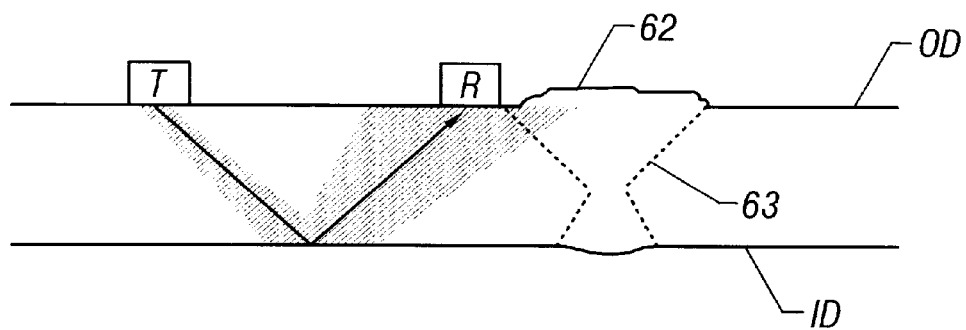
FIGS. 8A and 8B show the pitch-catch measurement technique used to obtain a reference signal/spectrum for examination of a double V-joint and single V-joint, respectively, weld/HAZ where the specimen is without internal cladding or weld overlay.
Figure 8B:
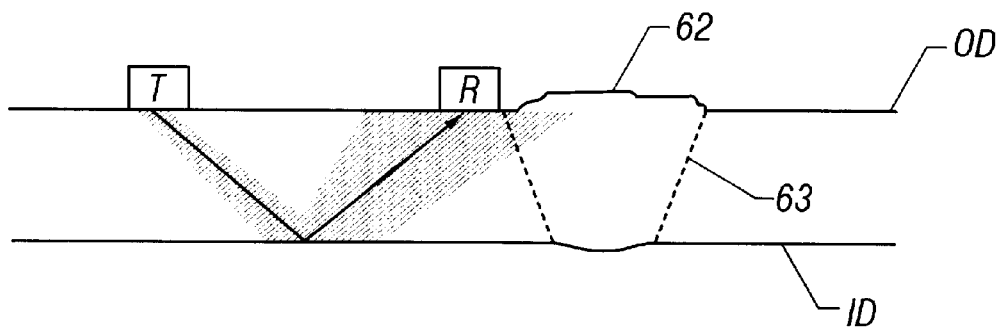

FIGS. 8A and 8B show the pitch-catch setup for obtaining a reference signal spectrum where the pipe or vessel under inspection is without cladding or weld overlay as in FIG. 6. The difference between FIG. 8 and FIG. 6 is that FIG. 6 uses only one transducer 64 and the sound beam will not come back unless there is an internal reflection of the sound wave. It just moves forward. In FIG. 8, even when there is no defect, a signal "pitched" by the transmitter T will be received because the forward signal is "caught" by the receiver R. The pitch-catch signal received by R is used to represent the effect of the material on the sound beam. Looking at FIG. 6 and FIG. 8, it is seen that the sound wave travels the same distance in each case. The only difference is in the direction. By comparing the two signals, the effect of attenuation due to material thickness can be eliminated.

Figure 9A:
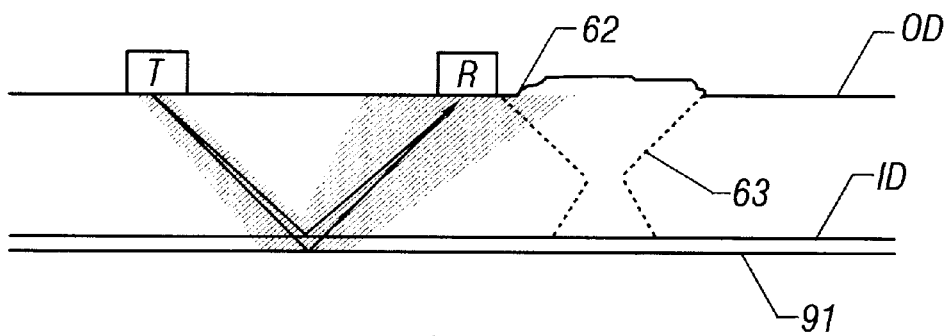
FIGS. 9A and 9B show the pitch-catch measurement used to obtain a reference signal/spectrum for examination of a double V-joint and single V-joint, respectively, weld/HAZ where the specimen has internal cladding or weld overlay.
Figure 9B:
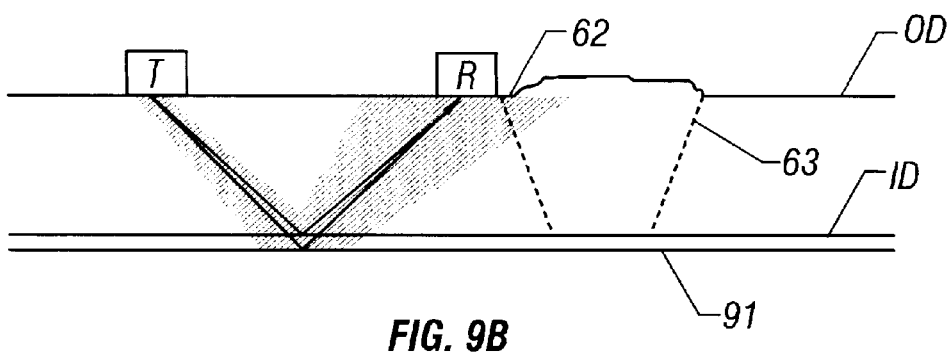

FIGS. 9A and 9B show the pitch-catch sound wave route/reflection where there is cladding or weld overlay 91 of the pipe or vessel being inspected.

Figure 10A:
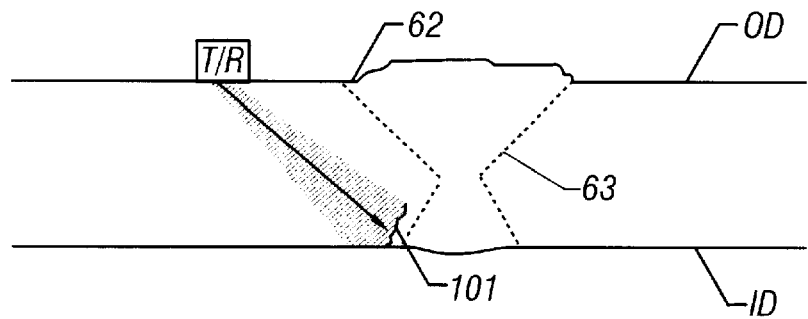
FIG. 10A and 10B show positioning of the transducer to maximize the signal amplitude of a defect for spectral analysis, as applied to a double V-joint and single V-joint, respectively, weld/HAZ where the specimen is without internal cladding or weld overlay.
Figure 10B:
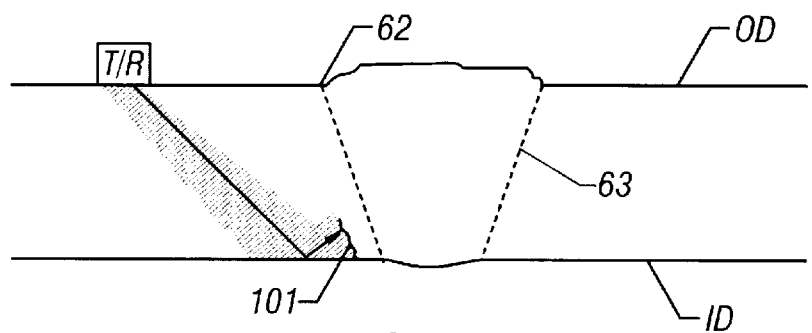
Figure 11A:
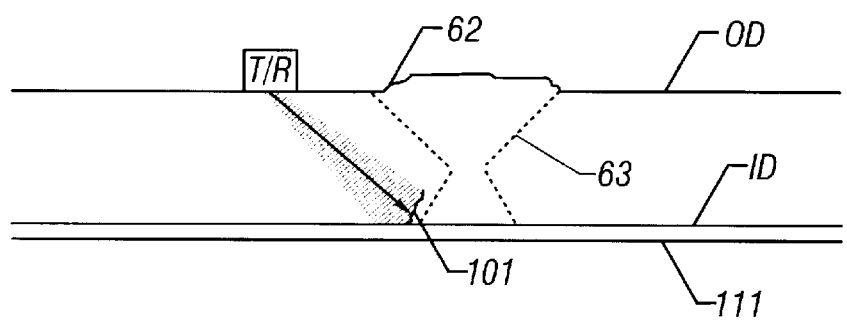
FIGS. 11A and 11B show positioning of the transducer to maximize the signal amplitude of a defect for spectral analysis, as applied to a double V-joint and single V-joint, respectively, weld/HAZ where the specimen has an internal cladding or weld overlay.
Figure 11B:
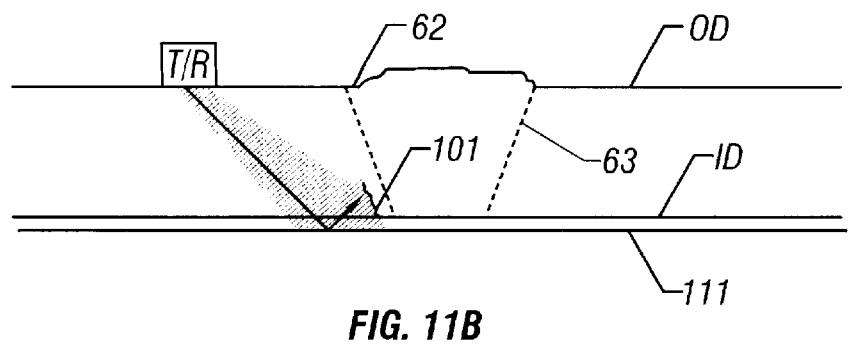

FIGS. 10A and 10B shows the positioning of the transducer to maximize the defect signal amplitude for ABSA in the cases where there is no cladding or weld overlay, but where a defect 101 has been detected along the heat affected zone. FIGS. 11A and 11B are the same as FIGS. 10A and 10B but for the case where there is a cladding 111 or weld overlay.

Figure 12:
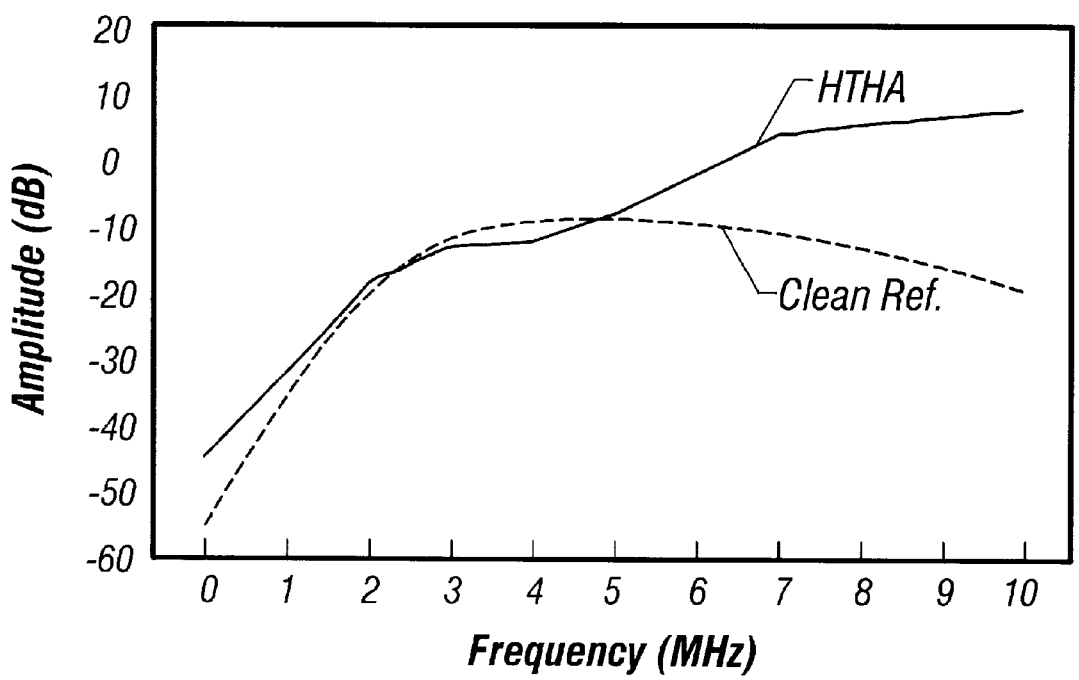
FIG. 12 shows the comparison of an HTHA spectrum with that of a clean reference.

FIG. 12 shows the comparison of the spectrum of a pulse-echo signal from localized HTHA in a weld/HAZ with that of a clean reference spectrum taken from the base metal next to the weld/HAZ.

Figure 13:
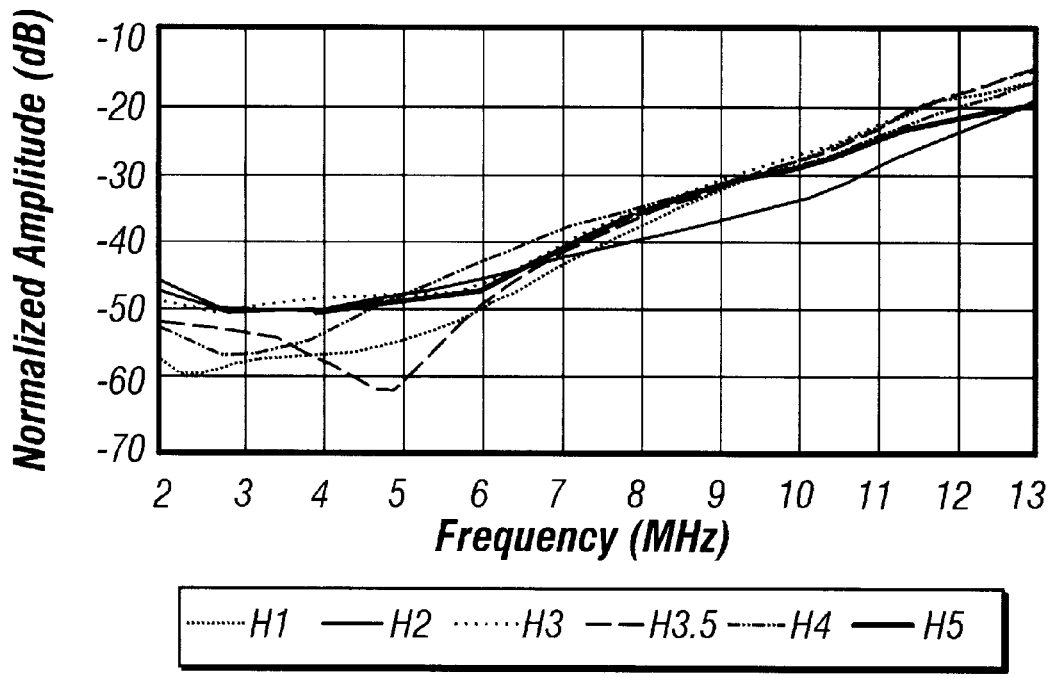
FIG. 13 shows typical deconvolved spectra from localized HTHA in a weld/HAZ.

FIG. 13 shows typical deconvolved spectra with normalized amplitude. This is the amplitude measured from the defect as determined in FIG. 10 minus the amplitude determined from FIG. 8. This is the solution to Equation (8) as subsequently shown. FIG. 13 shows deconvolved, normalized spectral curves from six measurements taken at six weld locations having different extent of HTHA damage. It should be noted that it is the trend that is of interest as opposed to the difference between the individual curves.

Figure 14:
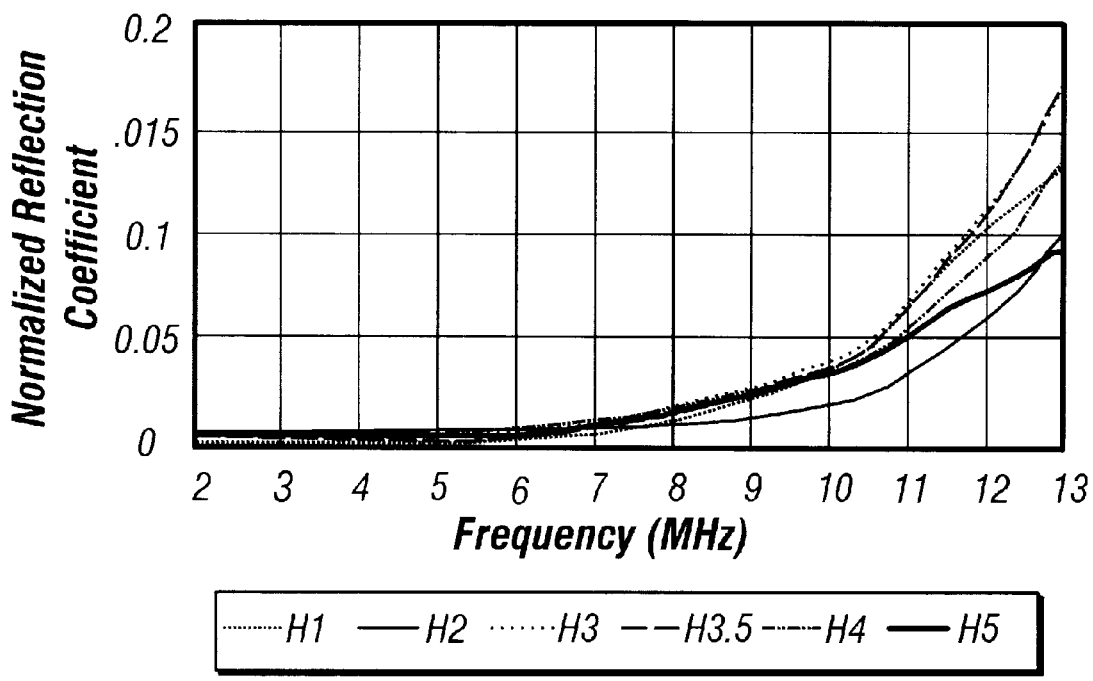
FIG. 14 shows typical reflection coefficients measured from localized HTHA in a weld/HAZ.

FIG. 14 shows the typical normalized reflection coefficient measured from localized HTHA in a weld/HAZ. The data were computed from the deconvolved spectra shown in FIG. 13 using Eq. (9).

FIGS. 15A–D show the ultrasonic technique for detecting localized high temperature hydrogen attack in a weld/HAZ. Welding defects and inclusions give ultrasonic signals similar to the reference signal, which can be discriminated from HTHA by their different frequency dependencies, as shown in the Amplitude vs. Frequency plot of FIG. 12. The above data (FIG. 12) were measured from a piece of ¾"-thick carbon steel pipe containing 78-mil-deep, localized HTHA in the HAZ in a pulse-echo mode. Typically, as shown in FIG. 15A, one transducer operated in a pulse-echo mode is used to detect defects in the weld/HAZ. If a reflection due to existence of a defect is observed, a time-of-flight signal as shown in FIG. 15B is obtained. That signal could be due to high temperature hydrogen attack in the weld/HAZ as shown, or it could also be caused by welding defects, such as lack of fusion, undercut, porosity, etc. That is, the signal may actually represent high temperature hydrogen attack in the HAZ, or it may only represent an original fabrication defect that has existed for a long time and should not cause any concern. In order to discriminate and determine the character of the defect, a clean reference is taken from the same base metal with identical transducers. By identical, it is meant that they have similar acoustic responses. The first part of the procedure is probe selection, and probes must be selected such that their ultrasonic responses are within tolerance range. If they are about the same, then the second step is to ensure that the electronic system will give a similar response from the pulse-echo mode and the pitch-catch mode because the circuitry is different for the pulse-echo and for the pitch-catch. The system's pulse-echo instrument system circuitry and pitch-catch instrument circuitry must be within the tolerance range. This is all done before the field inspection. The probes and system are calibrated together and only needs to be repeated periodically, say once per year. Then a clean reference is chosen (FIG. 15C) and will give a signal such as that shown in clean reference FIG. 15D. FIG. 12 compares these two signals, the HTHA spectrum being shown as a solid line and the clean reference being shown as the dashed line. The spectrum of the clean reference has been adjusted so that they match in the low frequency portion of the curves. The absolute amplitude of the signals is not of interest. What is of interest is the frequency dependence of the signal amplitude. With reference to the clean reference spectrum, the amplitude of the HTHA spectrum will increase in frequency. Welding defects much larger than HTHA fissures (typically 20–40 microns) exhibit a frequency dependence similar to the clean reference.

Table 3 shows instrument settings for the LeCroy digital oscilloscope for a signal averaging that is usually done prior to performing a spectrum analysis. Comparable equipment may be used, however it will be appreciated that settings will change accordingly.

Table 4 gives the settings of the LeCroy digital oscilloscope for performing a Fast Fourier Transform.

Table 6 shows alternative settings.

Software Specification

A computer program for performing data analysis is highly desirable. The following specifies the requirements for software where the LeCroy digital oscilloscope is used.

1. Download time domain data from a LeCroy digital oscilloscope to a PC.

2. Display the data on the PC as an Amplitude vs. Time graph with appropriate units indicated.

3. Show two arrows, or two vertical bars, overlaid with the above graph for the user to mark the portion of the original data to be extracted for further processing.

4. Adjust the size of the time window for FFT based on the user's input. Put the extracted data at the center of the window. Add zeros, if necessary, to fill the time window (i.e., zero padding) for FFT.

5. Transform the entire window from time to frequency domain. Show both Amplitude vs. Time and Amplitude vs. Frequency graphs on screen. Update the spectrum in real time as the user moves the arrows, or the vertical bars, in the time domain.

6. Store the spectrum in ASCII, or spreadsheet, or binary format, as chosen by the user. Allow retrieval of previously stored spectra to the active Amplitude vs. Frequency graph for comparison.

7. Allow up to four pairs of arrows in the Amplitude vs. Time graph to mark signals of the above FFT process. Display, in real time, all the corresponding spectra in the Amplitude vs. Frequency graph with proper legends.

8. Allow screen dump to a printer (black and white, or color, or both).

The program developed from the above specification may be obtained from Shell Oil Company.

Table 1 shows the number and type of 10 MHz transducers needed for this procedure for the base metal thickness determined. The base metal thicknesses correspond to the thickness of the vessel or pipe that was measured. So, when an inspection is to be performed, the thickness of the pipe or vessel is known and it is simply a matter of selecting the proper transducer for that inspection job. For example, for a 1-inch thick material, the second row of Table 1 shows that two shear-wave transducers, either 45° or 60°, and one creeping wave transducer are needed. The diameter of the transducers should be ¼ inch and the type of transducer should be a wide-band transducer. It does not have to be focused since the material is less than 1.2 inches thick, so the focal depth does not apply. For a 2-inch thick vessel, the fourth row, which is from 1.8 inch to 2.2 inches, shows that two 45° shear-wave transducers and one creeping wave transducer are needed. They should be wide-band transducers and they should be focused transducers with focal depth equal to 2.0 inches which also corresponds to a focal length of 2.8. The focal length is the actual sound path in the material. Focal depth is measured straight down from all the surfaces and, because of the angle, there is a difference. The manufacturer of the transducers is not critical so long as they meet the required specifications, i.e., diameter, band-width, focal length, focal depth, angles, etc.

Table 2 shows the pulser-receiver settings for a Panametrics Pulser-Receiver Model 5055PR. It will be appreciated that these settings will change depending on equipment used.

Table 6 shows the sensitivity level that is needed and the alternative threshold settings. This allows for adjustment of gain, and increasing the gain will give the proper sensitivity level again to compensate for amplitude drop due to an increase of material thickness. For example, for a 0.3-inch to 0.8-inch thick material, a 0.5-inch thick 90° calibration block corner is used for calibration. The calibration block of FIG. 2 is required for measuring the calibration of defects at different depths. For a 5-inch thick reactor shell requiring inspection, a calibration block that has a defect at 5 inches below the surface is required for accuracy. A one-inch block can be used to inspect the five-inch-thick material; however, one must know the difference between one inch and five inches so the calibrations can be adjusted back to five inches.

The compensation gain in Table 6 provides that difference. Everything is compared to one inch. So, if a one-inch thick material is being inspected, there is no compensation gain. But if a one-inch-thick calibration block is used to inspect a five-inch-thick material, then there is a difference between the calibration at 1.0 inch and the actual material being inspected; therefore there must be a compensation for the difference. To calibrate for five-inch-thick material the calibration at 4.8 inches is used. The amplitudes from the 4.8 inch and the 1.0 inch deep calibration defects are measured. The difference between these two gives the compensation gain. The additional compensation gain is added back to obtain the actual sensitivity of the five-inch block.

Table 5 shows the threshold level required for initial scanning. For example, if five-inch thick material is inspected, the calibration defect at 4.8 is used and the calibration is compared to a 90° corner. Anything within 52 dB of a 90° corner-reflector is reportable as a defect. If a 1/16-inch side-drilled (SDH) hole is used, then everything within 26 dB of the side-drilled hole signal is reportable.

Table 7 shows typical characteristic signal responses for what is considered a "suspect" signal. This is simply reference material to give one some idea of what to look for when the signals appear.

1. DETAILED PROCEDURE 1.1 The following describes a procedure for ultrasonic inspection of pressure vessels and piping systems for localized high temperature hydrogen attack (HTHA) in welds and heat-affected zone (HAZ).

1.2 The inspection procedure includes techniques for:
  (1) detection of localized HTHA,
  (2) discrimination of localized HTHA from other flaws that may be present in the weld and HAZ, e.g., inclusions and weld defects (i.e. slag, porosity, lack of fusion, undercut,) and
  (3) measurement of depth of localized HTHA.

1.3 This procedure is applicable to inspecting pressure equipment of nominal thickness up to and including 5.5 inch (140 mm).

2. REQUIRED INSTRUMENTS AND MATERIALS 2.1 The following items are required for performing inspections per this procedure:
  (1) a digital oscilloscope, such as LeCroy 9245, which can perform temporal averaging and Fast Fourier Transform (FFT),
  (2) a pulser/receiver which has a 3-dB-bandwidth from 1 MHz to 20 MHz and can provide up to 60 dB gain in signal output. Panametrics pulser/receiver 5055 PR can be modified to provide the required functions.
  (3) one pair of two 10 MHz, angle-beam, shear-wave transducers for each thickness range shown in Table 1,
  (4) one 10 MHz, straight-beam, longitudinal wave transducer,
  (5) ultrasonic couplant, such as Ultrajel II,
  (6) one calibration block 10 as shown in FIG. 1, made of the same grade of material as the one to be inspected, which contains one 1/16"-diameter, side-drilled hole (SDH) 11, one 1/8"-deep EDM notch electrical discharge machining (EDM) notch 12, and a 90° corner 13. Calibration block 10 includes a side 10' having a width of 1.0 inch and a side 10" having a width of 1.45 inches, and
  (7) one calibration block 20 as shown in FIG. 2, made of the same grade of material as the one to be inspected, which contains 1/16"-diameter SDHs H1–H8 at 0.5", 1.0", 1.5", 2.0", 2.5", 3.2", 3.9", and 4.8" below the surface, respectively, below and horizontal to the surface 20'. Calibration block 20 includes notches or steps S1–S8 corresponding to the relative positions of holes H1–H8.

2.2 The following items are optional:
  (1) a portable computer, such as a notebook PC, with a PCMCIA-GPIB card and a cable from the LeCroy GPIB to the computer's PCMCIA, if a PC program is used as the spectral analysis software. The PCMCIA card and the cable can be ordered from National Instruments.
  (2) spectral analysis software, such as a PC program, that can perform windowed FFT with zero padding. Such software can be obtained from Shell Oil Company.
  (3) one 10 MHz creeping wave transducer for each thickness range shown in Table 1.

one 10 MHz creeping wave transducer for each thickness range shown in Table 1.

3. SURFACE PREPARATION REQUIRE FOR FIELD INSPECTION 3.1 The areas to be examined shall have a surface finish no coarser than 125 grit Flapper wheeling the inspection surface (not including the OD weld crown) is recommended.

Grinding flush the weld crown is not required for inspecting weld and HAZ for localized HTHA per this procedure

4. PREPARATION PRIOR TO FIELD INSPECTION

The purpose of this section is to ensure that one can compare results of the pulse-echo measurements with those of the pitch-catch measurements without being affected by the differences between the transmitting and receiving transducers or between the pulse-echo and pitch-catch modes of the pulser-receiver. This requires carrying out two tasks: (1) matching the two transducers for pulse-echo and pitch-catch measurements, and (2) making sure that the impulse response of the pulser-receiver for pulse-echo measurement is the same as that for pitch-catch measurement. The former can be done by taking steps in Section 4.1 and the latter in Section 4.2. Both shall be conducted in the laboratory, i.e., prior to the field inspection.

TABLE 1

Shear Wave And Creeping Wave Transducers Needed For Inspection Per This Procedure

| | 10 MHz Transducer | | | | | | | |
|---|---|---|---|---|---|---|---|---|
| | Shear Wave | | Creeping Wave[1] | | | | | |
| Base Metal Thickness | Number of probes | Angle (degree) | Number of Probes | Diameter | Frequency Bandwidth | Focused Probe[2] | Focal Depth[3] | Focal Length[3] |
| 0.3"–0.8" | 2 | 45 or 60[4] | 1 | 0.25" | Wide-band | No | N/A | N/A |
| 0.8"–1.2" | 2 | 45 or 60[4] | 1 | 0.25" | Wide-band | Yes[1] | 1.0" | 1.4" |

TABLE 1-continued

Shear Wave And Creeping Wave Transducers Needed For Inspection Per This Procedure 10 MHz Transducer

| Base Metal Thickness | Shear Wave | | Creeping Wave[1] | | | | | |
|---|---|---|---|---|---|---|---|---|
| | Number of probes | Angle (degree) | Number of Probes | Diameter | Frequency Bandwidth | Focused Probe[2] | Focal Depth[3] | Focal Length[3] |
| 1.2"–1.8" | 2 | 45 | 1 | 0.375" | Wide-band | Yes | 1.5" | 2.1" |
| 1.8"–2.2" | 2 | 45 | 1 | 0.375" | Wide-band | Yes | 2.0" | 2.8" |
| 2.2"–2.9" | 2 | 45 | 1 | 0.5" | Narrow-band | Yes | 2.5" | 3.5" |
| 2.9"–3.5" | 2 | 45 | 1 | 0.5" | Narrow-band | Yes | 3.2" | 4.5" |
| 3.5"–4.3" | 2 | 45 | 1 | 0.75" | Narrow-band | Yes | 3.9" | 5.5" |
| 4.3"–5.3" | 2 | 45 | 1 | 1.0" | Narrow-band | Yes | 4.8" | 6.8" |

[1]Optional (i.e. not a mandatory requirement).
[2]Spherically focused, single-element transducer.
[3]Focal depth (FD) is measured from the surface straight down to the focal point. Focal length (FL) is measured from the entry point to the focal point along the sound path. FD = FL · cos(θ), where θ is the shear wave refraction angle in steel.
[4]Use 60° only if the OD weld crown is too wide to permit good inspection coverage with a 45° transducer.

4.1 Evaluation/selection of Transducers 4.1.1 Use one 10 MHz, shear-wave transducer and the 1" thick calibration block 10' shown in FIG. 1 to set up for pulse-echo measurements, as shown in FIG. 3. Apply pulser-receiver settings as given in Table 2 (for Panametrics pulser/receiver 5055PR.)

TABLE 2

Pulser-Receiver Settings
(Applied to Panametrics Pulser-Receiver 5055PR)

| Rep Rate | 1 KHz |
|---|---|
| Energy | 3 |
| Damping | 25 |
| Gain | 60 dB |
| H.P. Filter | 1 MHz |

4.1.2 Position the transducer to maximize the amplitude of the echo from the 90° corner 13, as shown in FIG. 3. Use the waveform test and/or 6 dB test below to adjust the RCVR ATTEN knob of the pulser/receiver until the signal has the maximum voltage without saturation. Record the RCVR ATTEN value as $RA_1$ in dB.

(1) Waveform Tests: Adjust the Amplitude knob on the oscilloscope to keep the peak of the signal of interest lower than the full screen height. Increase the RCVR ATTEN and adjust the amplitude knob to keep the peak within 20%–100% of the full screen height. The signal is not saturated when further increase of the RCVR ATTEN changes only the amplitude but not the waveform of the signal.

(2) 6 dB Test: Adjust the Amplitude knob on the oscilloscope to keep the peak of the signal of interest within 40%–100% of the full screen height. Increase the RCVR ATTEN of the pulser/receiver by 6 dB. The signal is saturated if the peak does not drop to half of its level before the increase of RCVR ATTEN.

4.1.3 Perform temporal averaging, per settings given in Table 3, to average the corner echo.

4.1.4 Perform FFT, per settings shown in Table 4, to obtain the spectrum of the averaged signal in dB. Store the spectrum of the pulse-echo signal as $PE_1(f)$.

TABLE 3

LeCroy Digital Oscilloscope Settings
For Use Of Temporal Averaging Per This Procedure
Definition Of Function E

| Class: | Average |
|---|---|
| Type: | Summed |
| Max number of points: | 50000 |
| Source: | Channel 1 |
| Max number of sweeps: | 200 |
| Artifact rejection: | Off |
| Dither: | Off |

4.1.5 Use another 10 MHz, shear wave transducer of the same kind. Repeat steps 4.1.2–4.1.4. Record the RCVR ATTEN value as $RA_2$ in dB, and store the spectrum of pulse-echo signal as $PE_2(f)$.

4.1.6 Determine the difference between the two spectra as a function of frequency by using the following equation:

$$\Delta(f)=[PE_1(f)+RA_1]-[PE_2(f)+RA_2] \quad (1)$$

If the difference $\Delta(f)$ is no more than 5 dB (i.e. $\Delta(f) \leq 5$ dB) throughout the frequency range from 3 MHz to 10 MHz, the two probes can be used as a pair for the following inspection. If the difference is greater than 5 dB, repeat the above steps until a pair of two matching probes having no more than 5 dB difference in their spectra is obtained.

TABLE 4

LeCroy Digital Oscilloscope Settings For Use Of FFT Per This Procedure
Definition Of Function F

| Class: | Fourier Transform |
|---|---|
| Type: | Power Spectrum |
| Max number of points: | 50000 |
| Source: | Function E |
| Window Type: | Rectangular |
| Zero Suppression: | On |
| Multiplication factor: | 1.0 |
| Additive constant: | 0 |

4.2 Evaluation/selection of Pulser-receiver 4.2.1 Use the two 10 MHz shear wave transducers qualified per Section 4.1 and the 1" thick calibration block 10' shown in FIG. 1 to set up for pitch-catch measurements, as shown in FIG. 4. Apply pulser-receiver settings as given in Table 2 (for Panametrics pulser/receiver 5055PR).

4.2.2 Position the transducers to maximize the amplitude of the backwall signal. Use the waveform test and/or 6 dB test described in 4.1.2 to adjust the RCVR ATTEN knob of the pulser/receiver until the signal has the maximum voltage without saturation. Record the RCVR ATTEN value as $RA_{PC}$ in dB.

4.2.3 Perform temporal averaging, per settings shown in Table 3, to average the backwall signal.

4.2.4 Perform FFT, per settings shown in Table 4, to obtain the spectrum of the averaged signal. Store the spectrum of the pitch-catch signal as PC(f) in dB.

4.2.5 Determine the difference between the pitch-catch spectrum and the pulse-echo spectra by using the following equation:

$$S(f)=[PE_i(f)+RA_i]-[PC(f)+RA_{PC}] \quad (2)$$

where i=1 or 2, whichever can result in $S(f) \leq 5$ dB for 45° shear wave transducers, or $S(f) \leq 30$ dB for 60° shear wave transducers. That is, the pitch-catch spectrum shall be within 5 dB of one of the two pulse-echo spectra throughout the frequency range from 3 to 10 MHz for 45° shear-wave transducers. For 60° shear wave transducers, the difference shall be less than 30 dB throughout the frequency range from 3 to 10 MHz.

4.2.6 If the system difference S(f) is greater than 5 dB for 45° shear wave (or 30 dB for 60° shear wave), reverse the transmitter and receiver (i.e., use the transmitting transducer as the receiver and the receiving transducer as the transmitter) in 4.2.1. Repeat steps 4.2.2–4.2.5. If the difference is still greater than the tolerance after reversing the transducers, try another pulser-receiver and repeat 4.1 and 4.2.1–4.2.5 until the difference is within 5 dB.

4.2.7 Use the transducer whose pulse-echo spectrum gives the smaller S(f) in 4.2.5 as the transmitting transducer for both pitch-catch and pulse-echo measurements, and the other transducer as the receiver for pitch-catch measurements, in field inspection.

4.2.8 Record the accepted PC(f), $PE_1(f)$, $PE_2(f)$, and S(f).

5. FIELD INSPECTION

The following inspection sequence is graphically presented by the logic tree shown in FIG. 5. Reference numbers shown on FIG. 5 correspond to the paragraph numbers herein.

5.1 Thickness Measurement and Probe Selection 5.1.1 Use a straight-beam, longitudinal wave transducer to measure the thickness of base metal next to the weld to be inspected. This can be done, for example, by measuring the time between the first and second backwall echoes and using the following equation to calculate the thickness $$h = \frac{5.96 \cdot \Delta t_{hl}}{2} \quad (3)$$

where h is the base metal thickness in mm, and $\Delta t_{hl}$ is the time between the first and second backwall echoes in µsec.

5.1.2 Use the measured base metal thickness and Table 1 to select two 10 MHz shear wave transducers which are qualified per Section 4 for the following inspection.

5.2 Setting Scanning Sensitivity Level and Time Window 5.2.1 Use one 10 MHz shear wave transducer selected per 5.1.2 and 4.2.7 for pulse-echo measurements with pulser-receiver settings given in Table 2.

5.2.2 Use one of the following two methods to set the gain/attenuation of the pulser-receiver.

(1) Use the calibration block 20 shown in FIG. 2: Select a calibration defect per the base metal thickness and Table 5. For example, to inspect a 5" thick vessel, one can use a 1/16" SDH H8 located at 4.8" below the surface 20' for calibration. Position the transducer and adjust the RCVR ATTEN of the pulser-receiver until the pulse-echo signal from the calibration defect is maximized without saturation. Adjust the oscilloscope to display the signal amplitude at 20% full screen height. Decrease the RCVR ATTEN by the number of decibels shown in Table 5 for the corresponding defect and depth. For example, reduce the RCVR ATTEN by 26 dB for inspection of a 5" thick vessel when H8, a 1/16" SDH at 4.8" below the surface 20' is used for calibration.

(2) Use the calibration block 10 shown in FIG. 1: Position the transducer and adjust the RCVR ATTEN of the pulser-receiver until the pulse-echo signal from one of the calibration defects (e.g., the 1/16" SDH 11 at 1" below the surface) is maximized without saturation. Adjust the oscilloscope to display the signal at 20% full screen height. Decrease the RCVR ATTEN by the number of decibels shown in Table 6 for the corresponding defect and base metal thickness. For example, reduce the RCVR ATTEN by $(26+H_{4.8})$ dB for inspection of a 5" thick vessel if a 1/16" SDH H2 located at 1" below the surface is used for calibration. [Note: $H_{4.8}$ is the compensation gain required to offset the thickness effect due to the difference between calibrating at 1" and 4.8"]. A procedure for measurements of compensation gain is as follows:

TABLE 5

Threshold Level Used For Detection Of Defects In The Initial Scanning

| Base Metal Thickness | Reference Depth | Threshold Level (relative to reflection from calibration reference*) | | |
|---|---|---|---|---|
| | | 90° Corner | 1/8" EDM Notch | 1/16" Side-drilled Hole |
| 0.3"–0.8" | 0.5" | −52 dB | −42 dB | −26 dB |
| 0.8"–1.2" | 1.0" | −52 dB | −42 dB | −26 dB |
| 1.2"–1.8" | 1.5" | −52 dB | −42 dB | −26 dB |
| 1.8"–.2" | 2.0" | −52 dB | −42 dB | −26 dB |
| 2.2"–2.9" | 2.5" | −52 dB | −42 dB | −26 dB |
| 2.9"–3.5" | 3.2" | −52 dB | −42 dB | −26 dB |
| 3.5"–4.3" | 3.9" | −52 dB | −42 dB | −26 dB |
| 4.3"–5.3" | 4.8" | −52 dB | −42 dB | −26 dB |

(3) Procedure for Measurement of Compensation Gain

This procedure should be used in the laboratory to set up Table 6 for alternative threshold settings.

(a) For each compensation gain shown in Table 6, use a transducer selected per Section 4.2.7 for the following measurements. For example, to determine the value of $H_{4.8}$ in Table 6, one should use a transducer that has a focal depth at 4.8 as shown in Table 1, and the transducer shall be a qualified transmitting transducer per section 4.2.7.

(b) Place the transducer on the calibration block shown in FIG. 2 for pulse-echo measurements. Position the probe so that the signal from the calibration defect of interest is maximized. For example, to get $H_{4.8}$, one needs to maximize the signal from the 1/16-inch SDH H8 located at 4.8 inches below the surface.

(c) Adjust the RCVR ATTEN so that the signal has an amplitude about 80% full screen height and is not saturated. Record the RCVR ATTEN value in dB as $RA_{ca12}$.

(d) Without changing instrument settings, move the probe to the calibration block 10 shown in FIG. 1. Position the probe so that the signal from the same type of calibration defect, which is now at 1 inch below the surface, is maximized. For example, to get $H_{4.8}$, one now needs to maximize the signal from the 1/16 inch SDH 11 at 1 inch below the surface on the calibration block 10 shown in FIG. 1.

(e) Adjust the RCVR ATTEN so that the signal has an amplitude about 80% full screen height and is not saturated. Record the RCVR ATTEN value in dB as $RA_{ca11}$.

(f) The compensation gain of interest is equal to $RA_{ca11} - RA_{ca12}$. For example, in applying the above steps for $H_{4.8}$, if one gets $RA_{ca12}$=2 dB and $RA_{ca11}$=30 dB, then one has $H_{4.8}$=30 dB-2 dB=28 dB.

5.2.3 Use the same calibration defect as used in 5.2.2 to find the point on the A-scan corresponding to sound waves entering the metal from the transducer shoe as follows:

(1) Position the transducer to maximize the defect signal.

(2) Place a cursor of the digital oscilloscope, say cursor #2, at the peak of the defect signal.

(3) Place another cursor, say cursor #1, at $\Delta t_{dcal}$ in front of cursor #2, where $\Delta t_{dcal}$ in μsec is calculated from $$\Delta t_{dcal} = \frac{2 \cdot d_{cal}}{3.24 \cdot \cos(\theta)} \quad (4)$$

The symbol $d_{cal}$ denotes the depth of the calibration defect in mm, and θ is the refraction angle of the shear wave. For example, if one uses the 1/16" SDH 11 of the calibration block 10 shown in FIG. 1 as the calibration defect, one should use $d_{cal}$=25.2 mm (i.e. 1 inch); and θ=45°, if a 45° shear wave transducer is used. Cursor #1 is now at the time corresponding to the transducer/metal interface, i.e. the OD of the equipment to be inspected. Do not move cursor #1 in the following inspection, except when sizing HTHA per Section 5.6. The above steps must be repeated if a different transducer or a different transducer shoe is used.

5.2.4 Move cursor #2 to the position which should correspond to the ID of the equipment. This can be done by placing cursor #2 at $\Delta t_{hs}$ behind the cursor #1, where $\Delta t_{hs}$ in μsec is computed from $$\Delta t_{hs} = \frac{2 \cdot h}{3.24 \cdot \cos(\theta)} \quad (5)$$

Do not move cursor #2 again in the following inspection. This step has to be repeated if the inspection moves from one area to another which has a different thickness.

5.3 Scanning for HTHA 5.3.1 Without adjusting the final instrument settings in 5.2, scan each side of the weld of interest, as shown in FIGS. 6 and 7. Look for signals above the threshold level (i.e. 20% full screen height). For double V-groove joints, examine signals in the first leg only. For single V-groove joints, examine both the first-leg and the second-leg signals. As shown in the figures, the scan shall cover, as a minimum, the area on the ID surface or on the cladding interface (or weld overlay interface) from the weld center to the toe of the OD weld crown.

TABLE 6

Alternative Threshold Setting

| | | Compensation Gain[1] (required to off-set the thickness effect) | | | Threshold Level (relative to a cal. ref. at 1" below the surface) | | |
|---|---|---|---|---|---|---|---|
| Base Metal Thickness | Reference Depth | 90° Cal. Block Corner | 1/8" EDM Notch | 1/16" Side-drilled Hole | 90° Cal. Block Corner | 1/8" EDM Notch | 1/16" Side-drilled Hole |
| 0.3"–0.8" | 0.5" | $C_{0.5}$ dB | $N_{0.5}$ dB | $H_{0.5}$ dB | -52 0 $C_{0.5}$ dB | -42 - $N_{0.5}$ dB | -26 - $H_{0.5}$ dB |
| 0.8"–1.2" | 1.0" | 0 dB | 0 dB | 0 dB | -52 dB | -42 dB | -26 dB |
| 1.2"–1.8" | 1.5" | $C_{1.5}$ dB | $N_{1.5}$ dB | $H_{1.5}$ dB | -52 - $C_{1.5}$ dB | -42 - $N_{1.5}$ dB | -26 - $H_{1.5}$ dB |
| 1.8"–2.2" | 2.0" | $C_{2.0}$ dB | $N_{2.0}$ dB | $H_{2.0}$ dB | -52 - $C_{2.0}$ dB | -42 - $N_{2.0}$ dB | -26 - $H_{2.0}$ dB |
| 2.2"–2.9" | 2.5– | $C_{2.5}$ dB | $N_{2.5}$ dB | $H_{2.5}$ dB | -52 - $C_{2.5}$ dB | -42 - $N_{2.5}$ dB | -26 - $H_{2.5}$ dB |
| 2.9"–3.5" | 3.2" | $C_{3.2}$ dB | $N_{3.2}$ dB | $H_{3.2}$ dB | -52 - $C_{3.2}$ dB | -42 - $N_{3.2}$ dB | -26 - $H_{3.2}$ dB |
| 3.5"–4.3" | 3.9" | $C_{3.9}$ dB | $N_{3.9}$ dB | $H_{3.9}$ dB | -52 - $C_{3.9}$ dB | -42 - $N_{3.9}$ dB | -26 - $H_{3.9}$ dB |
| 4.3"–5.3" | 4.8" | $C_{4.8}$ dB | $N_{4.8}$ dB | $H_{4.8}$ dB | -52 - $C_{4.8}$ dB | -42 - $N_{4.8}$ dB | -26 - $H_{4.8}$ dB |

[1]Compensation Gain = Amplitude of signal from defect at 1" below the surface - Amplitude of signal from defect at a selected depth. For example, $H_{1.5}$ = (amplitude of signal from 1/16" side-drilled hole at 1" below the surface ) - (amplitude of signal from 1/16" side-drilled hole at 1.5" below the surface.)

5.3.2 Mark all the locations having signals above the threshold level. Choose the areas having the most dense distribution of signals above the threshold level along the weld for follow-up evaluation. If there is no signal above the threshold level, mark only the location having the strongest signal within the area examined for follow-up evaluation.

5.4 Angle Beam Spectrum Analysis (ABSA) for Flaw Characterization 5.4.1 Taking reference spectrum 1) Use two 10 MHz shear wave transducers selected per 5.1.2 and 4.2 for pitch-catch measurements.

2) As shown in FIGS. 8 and 9, place the two transducers next to the weld under examination. Align the transducers so that they are perpendicular to the weld.

a) In the case of inspecting equipment without internal cladding or weld overlay, use the backwall signal to get a reference spectrum, as shown in FIG. 8.

b) In the case of inspecting equipment having internal cladding or weld overlay, use either the ID signal or the interface signal, as shown in FIG. 9, depending on the defect signal to be evaluated in Section 5.4.2. If the defect signal is a second leg signal, use the ID signal to get a reference spectrum. If the defect signal is in the first leg, use an interface signal taken from a disbonded interface (i.e. where the interface signal is strong and the ID signal is lost) to get a reference spectrum.

c) Adjust the transducer spacing until the signal for reference spectrum is maximized. Adjust also the oscilloscope so that the A-scan window covers more than the first one half skip distance in the case of inspecting a double-V joint and one full skip distance in the case of inspecting a single-V joint.

3) Use the 6 dB method described in 4.1.2 to adjust the RCVR ATTEN such that the signal for reference spectrum is maximized but not saturated on the digital oscilloscope. Record the RCVR ATTEN value as $RA_{ref}$.

4) Perform temporal averaging, per settings given in Table 3 on the A-scan. Store the A-scan after temporal averaging.

5) Perform windowed FFT by using one or both of the following methods.
   a) Use a digital oscilloscope to perform windowed FFT.
      1) Window the signal of interest in the A-scan, e.g. by using the Expand A or Expand B of a LeCroy digital oscilloscope.
      2) Use settings given in Table 4 to perform FFT on the windowed signal.
   b) Use a computer program to perform windowed and zero-padded FFT and perform the following steps:
      (1) Window the signal of interest in the A-scan.
      (2) Pad zeros on both sides of the signal.
      (3) Perform FFT on the windowed and zero-padded signal.

6) Store the spectrum as a reference spectrum, $Ref(f)$.

7) Based on the scanning results in 5.3, go directly to 5.4.1 (2) if there is no signal above the threshold level for follow-up evaluation. Repeat steps (1)–(6) to obtain a second reference spectrum if there is any signal above the threshold level. Use the average of the two measured spectrums as the reference:

$$RA_{ref} = \frac{RA_{ref1} + RA_{ref2}}{2} \quad (6)$$

and $$Ref(f) = \frac{Ref_1(f) + Ref_2(f)}{2^{25}} \quad (7)$$

where $RA_{ref1}$ and $RA_{ref2}$ are the RCVR ATTEN values used to obtain the two reference spectra $Ref_1(f)$ and $Ref_2(f)$, respectively.

5.4.2 Analyzing spectrum of defect signal

1) Disconnect the cable to the receiver transducer. Switch the pulser/receiver to the pulse-echo mode. Adjust the oscilloscope so that the A-scan window covers more than the first one half skip distance.

2) For each of the areas chosen in 5.3.2, look for signals showing characteristics of HTHA and/or crack, as listed in Table 7. If there are signals above the threshold level, select at least two signals most likely related to HTHA and/or crack for further analysis. If there is no more than one signal above the threshold level, select at least one signal for further analysis, preferably the one having the highest amplitude and/or most likely related to HTHA and/or crack.

3) For each selected signal, position the transducer to maximize the signal amplitude, as depicted in FIGS. 10 and 11. Use the 6 dB method described in 4.1.2 to adjust the RCVR ATTEN until the signal is maximized but not saturated. Record the RCVR ATTEN value as RA.

4) Perform temporal averaging, with settings given in Table 3, on the A-scan. Store the A-scan after temporal averaging.

5) Perform windowed FFT as described in 5.4.1(5) on the signal. Store the resultant spectrum as $A(f)$.

6) Compare the spectrum with the reference spectrum(s) measured from the same side of the weld under examination. This can be done in one or both of the following two ways:

TABLE 7

| | Typical Signal Response | | | | | | |
|---|---|---|---|---|---|---|---|
| | Medium - Deep Crack | Shallow Crack | Medium - Deep HTHA | Shallow HTHA | Undercut, Lack of Fusion | Slag, Inclusion | Porosity |
| Shear Wave Signal Amplitude | medium | medium | medium–low | low | high | medium | high |
| Shear Wave Signal Frequency[1] | normal | normal | high | high | normal | normal–low | normal |
| Deconvolved Shear Wave Spectrum[2] | Amplitude does not increase with frequency | Amplitude does not increase with frequency | Amplitude increases with frequency | Amplitude increases with frequency | Amplitude does not increase with frequency | Amplitude does not increase with frequency | Amplitude does not increase with frequency |
| Shear Wave Signal Walking Distance[3] | long | long | long | short | short | short–long | short |
| Tip Signal (Shear Wave) | yes | yes | yes/no | no | no | no | no |
| ID Creeping Wave Signal | yes | yes | yes | yes | yes | no | no |
| 30-70-70 Signal | yes | no | yes | no | no | yes/no | yes/no |

TABLE 7-continued

Typical Signal Response

| | Medium - Deep Crack | Shallow Crack | Medium - Deep HTHA | Shallow HTHA | Undercut, Lack of Fusion | Slag, Inclusion | Porosity |
|---|---|---|---|---|---|---|---|
| Signals along the weld, continuously or intermittently | yes/no | yes/no | yes | yes | yes/no | yes/no | yes/no |

Note 1: See FIG. 7.
Note 2: See FIG. 8.
Note 3: See FIGS. 9 and 10.

a) Using a digital oscilloscope, one can display the spectrum of the defect signal and a reference spectrum on the same screen. Shift one spectrum relative to the other until the two spectrums are matched at a low frequency between 2 and 5 MHz. Examine the difference between the two spectrums above that frequency. Localized HTHA in weld HAZ should show a spectrum having an increase of amplitude with the increase of frequency relative to the reference spectrum, as shown in FIG. 12. Other defects that may exist in the same area (e.g., porosity, lack of fusion, undercut, slag, inclusions, and crack) should have about the same shape (i.e. frequency dependence) as that of the reference spectrum.

b) Using spectral analysis software, one can export the spectrums to a spreadsheet program. Perform deconvolution by using the following equation:

$$D(f) = A(f) + RA - [Ref(f) + RA_{ref}] - S(f) \quad (8)$$

where $D(f)$ is the difference in the spectral response between "defect" and "no defect", by taking the differences in RCVR ATTEN values, transducers, and the operated modes (i.e. pulse-echo or pitch-catch) out of the picture. Localized HTHA in weld/HAZ is unique in that its deconvolved spectrum has an increase of amplitudes with frequency, as shown in FIG. 13. Other defects in the same area (such as cracks, inclusions, and weld defects) have deconvolved spectra showing amplitudes independent of the frequency. Using the deconvolved result, one can further calculate a reflection coefficient by using the following equation:

$$C(f) = 10^{\frac{D(f)}{20}} \quad (9)$$

Localized HTHA in the weld/HAZ is unique in that its reflection coefficient increases with the increase of frequency, as shown in FIG. 14. Other defects in the same area produce reflection coefficients independent of the frequency.

5. 5 Use of Logic Tree to Determine Further Actions

Review results in 5.3 and 5.4 and use the logic tree given in FIG. 5 to determine further actions.

5.5.1 In the case where there is no signal above the threshold level (i.e., no "suspect" signal), review the result of ABSA done on the signal having the highest amplitude.

1) If the amplitude of the defect spectrum relative to the reference spectrum does not increase with the increase of frequency, there is no HTHA. Record the result for future reference.
2) If the amplitude of the defect spectrum relative to the reference spectrum increase with the increases of frequency, there may be very minor or no HTHA. Record the result for future reference.

5.5.2 In the case where one or more signals above the threshold are detected, examine the signal distribution along the weld.

1) If the signals are spotty (i.e., the defects have no length along the weld,) compare two reference spectrums with spectrums of defects signals that are above the threshold and most likely related to HTHA.
   a) If none of the defect spectrums relative to the reference spectrums shows an increase of amplitude with the increase of frequency, there is no HTHA. Record the results for future reference.
   b) If one or more of the defect spectrums are showing a relative increase of amplitude with the increase of frequency, there might be spotty HTHA. Record the results for future reference.
2) If the signals are somewhat continuous along the weld, compare two reference spectrums with spectrums of defect signals that are above the threshold and most likely related to HTHA and/or cracks.
   a) If none of the defect spectrums relative to the reference spectrums shows an increase of amplitude with the increase of frequency, there is no sign of HTHA fissures. Use crack detection and sizing techniques to determine whether there is any crack and to size any crack identified.
      (1) Report crack and its depth, for any crack detected and sized.
      (2) Record the results for future reference if there is no crack found.
   b) If one or more of the defect spectrums are showing a relative increase of amplitude with the increase of frequency, there is probably HTHA. Perform sizing of localized HTHA per Section 5.6.

5.6 Sizing Localized HTHA 5.6.1 Use the same pulse-echo settings as in 5.4.2(3). Position the transducer until the HTHA signal is maximized but not saturated.

5.6.2 Move the transducer forward (i.e. toward the weld) until the signal amplitude is at 50% of its maximum level.

5.6.3 Without further moving the signal, move cursor #1 to the peak of the signal. Record the time between cursor #1 and cursor #2 as $\Delta t_{HTHA}$.

5.6.4 Calculate and record the depth of HTHA by using the following equation:

$$d = \frac{3.24 \cdot \Delta t_{HTHA}}{2} \cdot \cos(\theta) \quad (10)$$

where $d_{HTHA}$ is the depth of HTHA in mm. (The depth of HTHA in inches is $d_{HTHA}/25.4$.)

5.6.5 Return cursor #1 to its previous position (i.e. back to the time corresponding to the OD surface) except when there is no additional measurement to be done.

What is claimed is:

1. A method for detecting high temperature hydrogen attack in a weld or heat-affected zone of a pipe or vessel comprising the steps of:
   a) obtaining the spectrum of a pulse-echo signal measured from a weld or heat-affected zone;
   b) obtaining the spectrum of a pitch-catch signal measured from the base metal adjacent to the weld or heat-affected zone;
   c) comparing the spectrum of said pulse-echo signal measured from the weld or heat-affected zone with the spectrum of said pitch-catch signal measured from the base metal adjacent to the weld or heat- affected zone; and
   d) determining from said comparison the presence or absence of high temperature hydrogen attack damage to said weld or heat-affected zone.

2. The method of claim 1 wherein said high temperature hydrogen attack in the weld or heat-affected zone manifests itself as a spectrum having an increase of amplitude with the increase of frequency relative to the reference spectrum measured from base metal in the pitch-catch mode.

3. The method of claim 1 further including the step of selecting ultrasonic transducers and instruments having similar spectral response in pulse-echo and pitch-catch measurements.

4. The method of claim 1 further including the step of using calibration blocks to ensure that the transducers/instruments are set at a proper sensitivity level to detect a high temperature hydrogen attack signal for said comparison in the frequency domain.

5. The method of claim 1 further including the step of eliminating artifacts by compensating for differences between pulse-echo and pitch-catch measurements.

* * * * *